(12) United States Patent
Mandziuk et al.

(10) Patent No.: US 7,256,576 B2
(45) Date of Patent: Aug. 14, 2007

(54) ID-OD DISCRIMINATION SENSOR

(75) Inventors: Michael William Mandziuk, Calgary (CA); Paul Douglas Gies, Redwood Meadows (CA)

(73) Assignee: General Electric Company, Schenectady, NY (US)

( * ) Notice: Subject to any disclaimer, the term of this patent is extended or adjusted under 35 U.S.C. 154(b) by 193 days.

(21) Appl. No.: 11/193,283

(22) Filed: Jul. 29, 2005

(65) Prior Publication Data
US 2007/0022830 A1 Feb. 1, 2007

(51) Int. Cl.
*G01N 27/90* (2006.01)
*F16L 101/30* (2006.01)
*F16L 55/40* (2006.01)

(52) U.S. Cl. .................................... 324/220; 324/222

(58) Field of Classification Search .... 73/865.8–865.9, 73/866.5; 324/220, 222, 228, 240
See application file for complete search history.

(56) References Cited

U.S. PATENT DOCUMENTS

| | | | |
|---|---|---|---|
| 4,016,130 A | | 4/1977 | Antczak |
| 4,049,396 A | | 9/1977 | Hiles |
| 4,227,350 A | | 10/1980 | Fitzer |
| 4,919,013 A | | 4/1990 | Smith et al. |
| 5,457,841 A | | 10/1995 | Minton |
| 5,600,240 A | * | 2/1997 | Mikhailovich et al. ..... 324/219 |
| 5,864,232 A | | 1/1999 | Laursen |
| 5,945,766 A | * | 8/1999 | Kim et al. ................... 310/268 |
| 6,847,207 B1 | | 1/2005 | Veach et al. |
| 2007/0028706 A1 | * | 2/2007 | Mandziuk et al. ......... 73/865.8 |

OTHER PUBLICATIONS

Bickerstaff, et al.; "Review of Sensor Technologies for In-Line Inspection of Natural Gas Pipelines"; Undated; Sandia National Laboratories; pp. 1-10, by Oct. 2005.
"Specification and Requirements for Intelligent Pig Inspection of Pipelines"; Version 3.2; Jan. 2005; pp. 1-28.
"MagneScan Triax Provides Greater Insight into Pipeline Defects"; General Electric Company, 2 sheets, by Jul. 18, 2005.
"MagneScan Specifications"; General Electric Company, Jul. 15, 2005; 2 sheets.

(Continued)

*Primary Examiner*—Thomas P. Noland
(74) *Attorney, Agent, or Firm*—James E. McGinness, Esq.; Armstrong Teasdale LLP (57) ABSTRACT

A sensor body for use in a pig for determining characteristics of a pipeline wall though which the pig passes includes a circuit board and a single coil wrapped around the circuit board. A microcontroller is mounted to the circuit board and connected to the single coil and configured to induce a waveform on the coil to thereby create an eddy current in the pipeline wall adjacent the sensor body. The microcontroller is also configured to measure changes in a characteristic of the induced waveform on the single coil that correspond to the presence of anomalies on an inside diameter of the pipeline wall. The sensor body also includes a sensor body cover molded about the circuit board, the microcontroller and the single coil. The sensor body cover consists essentially of a wear resistant, non-conductive material that includes a polymer material.

20 Claims, 7 Drawing Sheets

OTHER PUBLICATIONS

MagneScan Tool Data Sheet; General Electric Company; Issue 10; Sep. 6, 2002; 1 sheet.

MagneScan Trap Data Sheet; General Electric Company; Issue 7; Jan. 25, 2001, 1 sheet.

"Industry Documents"; Inline Inspection Association Webpage; Copyright 2003; 2 sheets.

"Welcome to the Inline Inspection Association"; Inline Inspection Association Webpage; Copyright 2003; 1 sheet.

* cited by examiner

ID-OD DISCRIMINATION SENSOR

BACKGROUND OF THE INVENTION

This present invention relates intelligent pigs used in oil and gas pipelines to diagnose defects in pipeline walls.

It is common practice to insert an intelligent pig into a pipeline and move the pig through the pipeline as an in-line inspection tool. The pig usually has urethane cups located in a front towing portion that seal with the pipeline wall and tow the intelligent portion of the pig through the pipeline by either gas or oil (fluids) in the pipeline pushing the cups as this product flows in the pipeline. The intelligent portion of the pig collects data concerning defects in the pipeline wall as it is towed through the pipeline. The information collected on these anomalies comprises, for example, the location, size and shape of cracks, pits, dents and corrosion in the pipeline wall. This information is stored in the pig and later retrieved from the pig when it is removed from the pipeline. This information can then be analyzed and the pipeline repaired as needed.

It is known for the intelligent pig in-line inspection tool to measure the magnetic flux leakage associated with defects in pipeline walls. The tool accomplishes this by magnetizing the pipeline wall and using sensors to measure the leakage field generated by any defects. The magnetic field is usually constant when no defects in the wall are present and as a result constant leakage is detected. When there is a defect in the wall, the magnetic field induced by the pig in the pipeline wall becomes more concentrated and increased leakage of magnetic fields develop which are measured to obtain information about the defect in the pipeline wall.

U.S. Pat. No. 6,847,207 issued Jan. 25, 2005 discloses an inspection tool that measures magnetic flux leakage in the pipeline wall caused by anomalies in the pipeline wall. Magnetic flux leakage measuring technology relies on hall effect sensors to measure the magnitude of the defect that causes the flux leakage to occur. The location of the defect in the pipe wall, that is closer to the inside diameter (ID) or outside diameter (OD) cannot be determined from magnetic flux leakage measuring technology due to the physics of the magnetic flux leakage paths around the defect. U.S. Pat. No. 6,847,207 teaches that ID/OD discrimination is accomplished by using an eddy current pulser coil and an eddy current detection coil, or a two coil pair, to provide a signal used to indicate whether a detected flux leakage anomaly is in the interior surface of the pipeline wall. However, the use of two coils, a pulser coil and a sensor coil, increases the size requirement of the sensor body and the associated circuitry required to pulse one coil and read the other coil.

BRIEF DESCRIPTION OF THE INVENTION

Therefore, one aspect of the present invention provides a sensor body for use in a pig for determining characteristics of a pipeline wall though which the pig passes. The sensor body includes a circuit board and a single coil wrapped around the circuit board. A microcontroller is mounted to the circuit board and connected to the single coil and configured to induce a waveform on the coil to thereby create an eddy current in the pipeline wall adjacent the sensor body. The microcontroller is also configured to measure changes in a characteristic of the induced waveform on the single coil that correspond to the presence of anomalies on an inside diameter of the pipeline wall. The sensor body also includes a sensor body cover molded about the circuit board, the microcontroller and the single coil. The sensor body cover consists essentially of a wear resistant, non-metallic material that includes a polymer material.

In another aspect, the present invention provides an instrument pig for analyzing anomalies in a wall of a pipeline. The pig includes a tow portion for moving the pig through the pipeline and an instrument portion for measuring anomalies in the pipeline wall. The instrument portion includes a plurality of arms disposed circumferentially around the instrument portion, each arm flexibly mounted on the instrument portion to allow the arm to move radially inwardly and radially outwardly to provide clearance for the pig in the event that it encounters obstructions as it travels through the pipeline. The instrument portion also includes a sensor body mounted to each arm. The sensor body includes a circuit board, a single coil wrapped around the circuit board and a microcontroller mounted to the circuit board and connected with the single coil for inducing a waveform on the coil to thereby create an eddy current in the pipeline wall adjacent to the sensor body. The microcontroller is configured to measure changes in a characteristic of the induced waveform on the single coil that correspond to the presence of anomalies on an inside diameter of the pipeline wall. The sensor body includes a sensor body cover molded about the circuit board, the microcontroller and the single coil. The sensor body cover consists essentially of a wear resistant, non-metallic material including a polymer material. The pig also includes magnets mounted on the arms for generating and transmitting a magnetic field through portions of the pipeline wall adjacent the sensor body. The pig further includes a data storage portion for storing data measured by the microcontroller.

DETAILED DESCRIPTION OF THE INVENTION

The present invention relates to a magnetic flux leakage sensor suitable for use in a pipeline inspection pig. The sensor comprises a plurality of magnetic flux sensing devices and a single ID/OD coil which is wrapped around the perimeter of a circuit board on which the magnetic flux sensing devices are mounted. The single coil wrapped around the circuit board instead of the customary two coils previously used increases the compactness of the sensor and reduces the circuitry associated with the two coils. A microcontroller is mounted on the circuit board and monitors the magnetic flux sensing devices to measure changes in the magnetic field in the pipeline wall and thereby detect anomalies in the pipeline wall. The microcontroller is also connected with the single coil to induce a waveform in the coil and create an eddy current in the inside wall of the pipeline. The microcontroller detects liftoff of the sensor from the inside wall of the pipe by measuring changes in a characteristic of the induced waveform in the single ID/OD coil. The detection of liftoff of the sensor from the pipeline wall at the same time as an anomaly is detected determines that the anomaly is on the inside wall of the pipeline. The sensor also comprises a non-conductive wear surface normally in contact with the inside wall of the pipeline that permits for an optimum amount of energy transfer in both directions between the single coil and the pipeline wall.

The non-conductive wear resistant surface may comprise a polymer material, such as, for example, a polyurethane filled with wear resistant particles. The wear resistant particles may comprise particles selected from the group consisting of silicon carbide and/or other non-conductive fillers.

The characteristic measured by microcontroller may be changes in peak-to-peak amplitude of the induced waveform.

In accordance with the present invention there is provided a sensor body for use in a pig for determining characteristics of a pipeline wall though which the pig passes. The sensor body comprises a circuit board, a single coil wrapped around the circuit board, and a microcontroller mounted to the circuit board. The microcontroller is connected with the single coil for inducing a waveform in the coil to thereby create an eddy current in the pipeline wall adjacent the sensor body. The microcontroller measures changes in a characteristic of the induced waveform on the single coil that correspond to the presence of anomalies on an inside diameter of the pipeline wall. The sensor body further comprises a sensor body cover molded about the circuit board, the microcontroller and the single coil. The sensor body cover consists essentially of a wear resistant, non-conductive polymer material.

Figure 1:
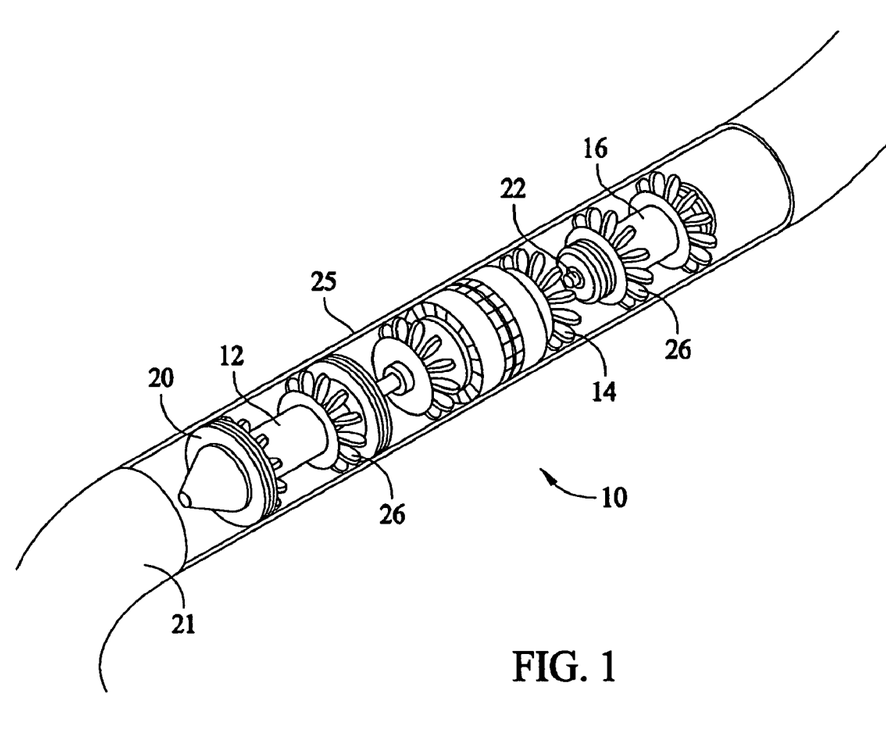
FIG. 1 is a diagrammatic illustration of an intelligent pig for analyzing anomalies in a pipeline wall according to an embodiment of the present invention.

Referring now to FIG. 1, an intelligent pig 10 is shown for analyzing anomalies in pipeline walls. The pig 10 comprises a tow portion 12, an instrument portion 14 and a data storage portion 16. Adjacent portions 12, 14 and 14, 16 are connected by a universal joint 22 that permits movement of the pig 10 around bends in the pipeline. In the embodiment shown, the tow portion 12 houses the batteries for providing electrical power to the pig. Annular cups 20 are mounted around the circumference of the tow portion for sealing the annulus between the tow portion 12 and the pipeline wall 21. It should be understood that the tow portion 12 may comprise multi-diameter cups that can expand and contract to conform with changes in the diameter of the pipeline. The flow of pipeline fluid, such as, for example, natural gas or oil is trapped by the cups causing the flowing fluid to push the pig through the pipeline.

The data storage portion 16 has a data memory for the pig 10. Data concerning the analysis of anomalies in the pipeline wall are transmitted from sensors contained in the instrument portion 14 for storage in memory. This data is analyzed after the pig is removed from the pipeline.

It should be understood that while the three portions of the pig are shown as separate sections interconnected by universal joints, in alternative embodiments, the pig 10 may comprise a single section that houses the battery, instruments, and memory.

Referring to FIG. 1, circumferentially spaced suspension wheels 26 are mounted at the ends of each portion 12, 14, 16 for engagement with the inside of the pipeline wall and, together with the cups 20, to stabilize the portions of the pig 10 relative to the pipeline wall.

Figure 2:
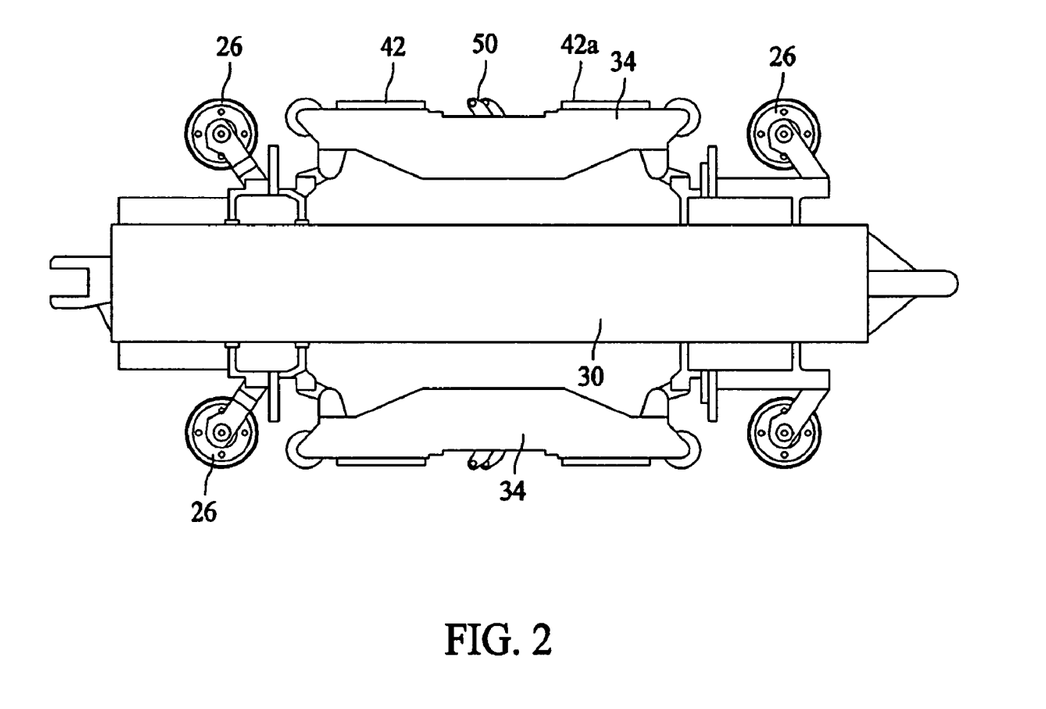
FIG. 2 is a side view of the instrument portion of the pig shown in FIG. 1.

Referring to FIG. 2, the instrument portion 14 of the pig 10 is shown to have a central body 30, which is supported by a plurality of circumferentially spaced apart suspension wheels 26 mounted adjacent opposing ends of the central body 30. The wheels 26 support the instrument portion 14 in the pipeline. Attached to the central body, for radial movement relative thereto, are a plurality circumferentially spaced apart arms 34. The radial movement of the arms 34 relative to the central body 30 provides clearance for the instrument portion 14 pig 10 in the event that it encounters obstructions as it travels through the pipeline.

Magnets 42, 42a of opposite polarity are mounted on the arms 34 on opposing sides of a sensor body 50 for generating and transmitting a magnetic field through portions of the pipeline wall 21 adjacent the sensor body 50.

Figure 3:
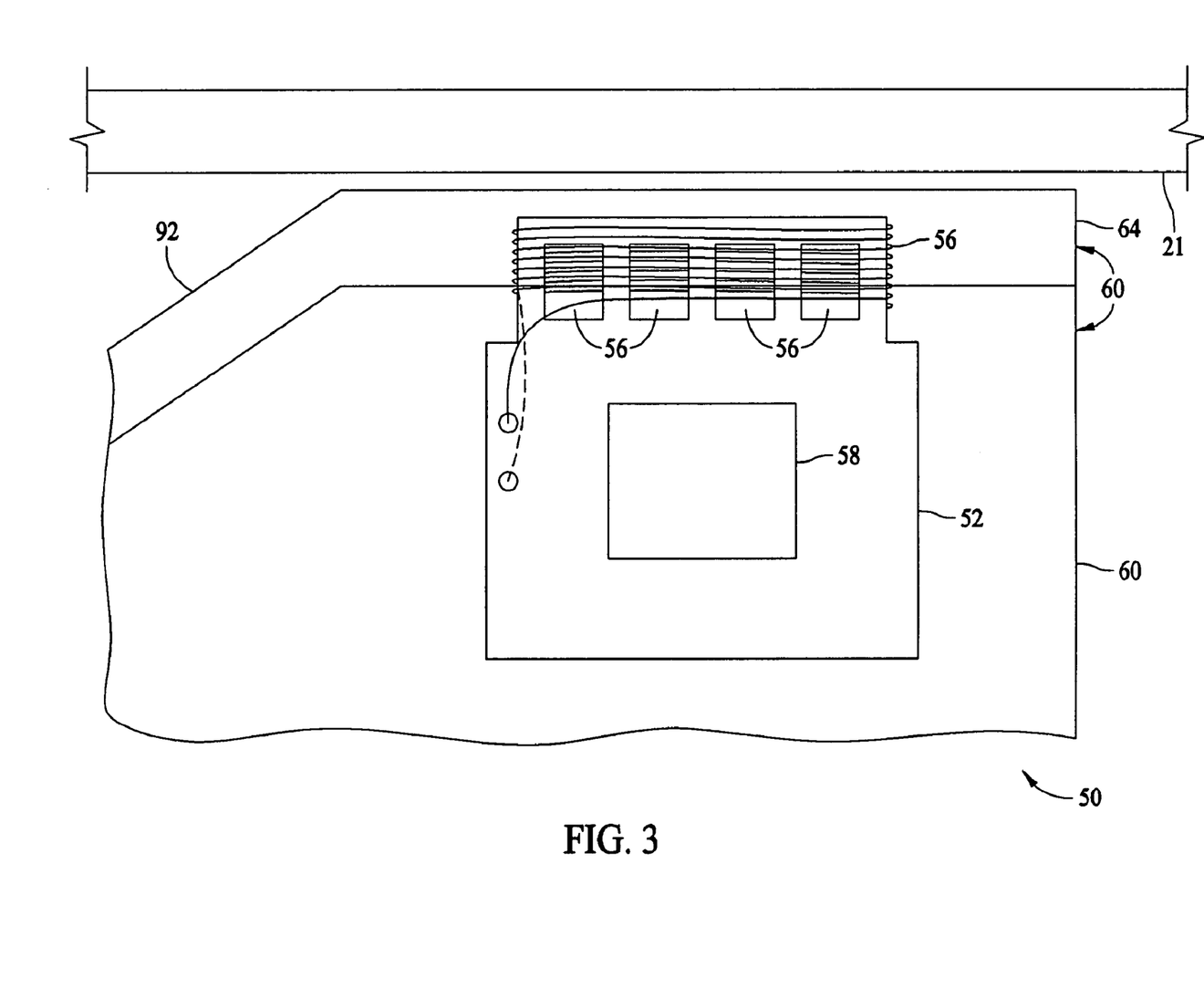
FIG. 3 is a cross-sectional view of a configuration of sensor body.

A sensor body 50 is mounted to each arm 34. As shown in FIG. 3, sensor body 50 comprises a circuit board 52, a single coil 54 wrapped around the circuit board 52, a plurality of magnetic flux leakage measuring devices 56 mounted on the circuit board 52, and a microcontroller 58 mounted to the circuit board 52. The microcontroller 58 is connected with the magnetic flux leakage measuring devices 56 for detecting flux leakage in the pipeline wall 21. The magnetic flux leakage devices 56 each comprise a hall effect sensing device. The microprocessor 58 is also connected with the single coil 54 for inducing a waveform on the coil 54 to thereby create an eddy current in the pipeline wall 21 adjacent the sensor body 50. The microcontroller 58 measures changes in the peak-to-peak amplitude of the induced waveform on the single coil 54 that correspond to the presence of anomalies on an inside of the pipeline wall. In some configurations, sensor body 50 further comprises a sensor body cover 60 comprising a sledge 64 and a bottom cover 66, both molded about circuit board 52, the microcontroller 58, the hall effect sensing devices 56 and the single coil 54. Sledge 64 consists essentially of a wear resistant, non-conductive polymer material, such as for example, polyurethane filled with a wear resistant filler such as silicon carbide and/or other non-conductive fillers. ("Non-conductive," as used herein, means "electrically non-conductive," unless otherwise explicitly stated. Another suitable non-conductive filler may include diamond chips.) Bottom cover 66 consists essentially of a polyurethane without the silicon carbide or other non-conductive fillers. For example, in some configurations, board 52, including hall effect sensing devices 56 and single coil 54 are placed in a mold and a mixture of uncured polyurethane and silicon carbide poured in up to the intended depth of sledge 64. This sledge is allowed to cure, and a polyurethane epoxy compound is poured on top of sledge 64 and allowed to cure to form bottom cover 66. Thus, sledge 64, in effect, forms a sort of "laminate" over the face of sensor cover 60 that provides hardness and extended wear resistance as pig 10 moves against pipe wall 21. (Indexing pins, not shown, can be used to hold circuit board 52 in place in the mold.)

In some configurations of the present invention, bottom cover 66 is homogeneous and, in its entirety, consists essentially of either polyurethane without silicon carbide or other fillers, or polyurethane with silicon carbide and/or other non-conductive fillers.

The use of silicon carbide or other hard, non-conductive fillers substantially increases the life of sensor bodies 50. In some configurations, 36 grit silicon carbide (SiC) particles pretreated with silane is used. (Silane washing can be performed by vendors of silicon carbide. Untreated SiC particles can also be used.) A suitable polyurethane resin used in some configurations is RenCast™ 6444/Ren®6444 polyurethane (available from RenShape Solutions, East Lansing, Mich.), which is a semi-rigid, amber, two component polyurea elastomer suitable for wear resistant applications. At an early stage of mixing the polyurethane resin, the SiC particles are added and mixed in thoroughly. In some configurations, the mixture is centrifuged and/or placed in a vacuum before use to remove air that may be trapped by the mixing. Any amount of 36 grit SiC in this material up to at least about 20% by weight increases the wear resistance and lifetime of sensor bodies 50, and particularly sledge 64, although in experiments, 10% by weight SiC has been found to outlast sledges 64 of 20% by weight SiC. In particular, tests on actual sensor bodies 50 using 10% by weight SiC in sledge 64 consistently showed less than 2.0 mm of abrasive wear after more than 236 km of run on a test track. In some test runs, about 1800 km of run on a test track produced 1.41 mm of wear or less. Sensor bodies having sledges of 20% by weight SiC produced 1.04 mm of wear or less after 686 km of run on a test track, as compared to 0.93 and 0.73 mm for two different sensor bodies having 10% by weight sledges. Sensor bodies without SiC were found to have wear of 1.4 and 1.2 mm after only 14 km.

In some configurations of the present invention, SiC (or other non-conductive filler) is also used for annular cups 20. For example, annular cups 20 in some configurations consist essentially of the same composition used for sledges 64. This composition advantageously reduces wear on annular cups 20.

Figure 4:
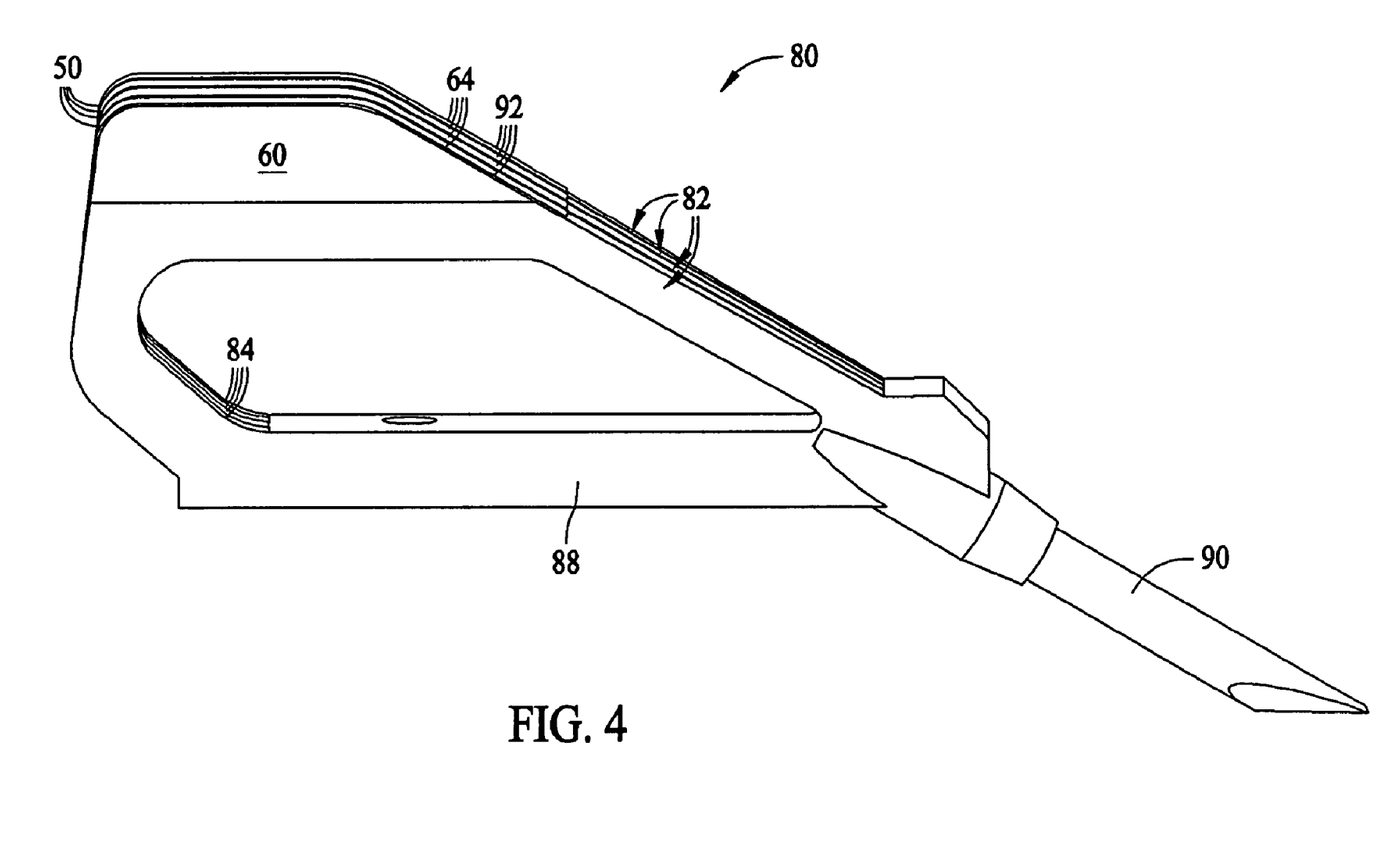
FIG. 4 is a perspective side view of a configuration of an assembly of a sensor block.
Figure 5:
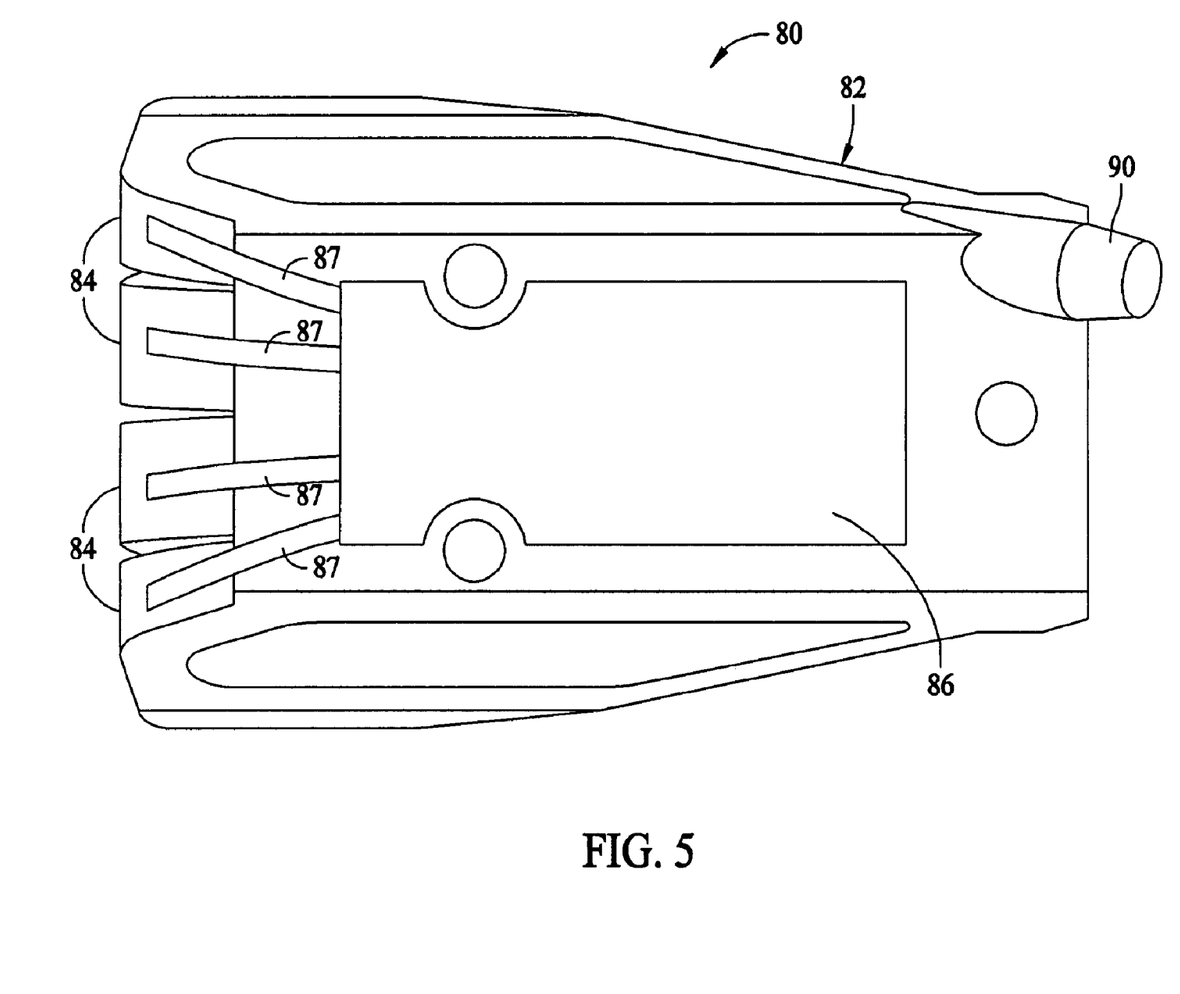
FIG. 5 is a bottom view of the sensor block configuration of FIG. 4.
Figure 6:
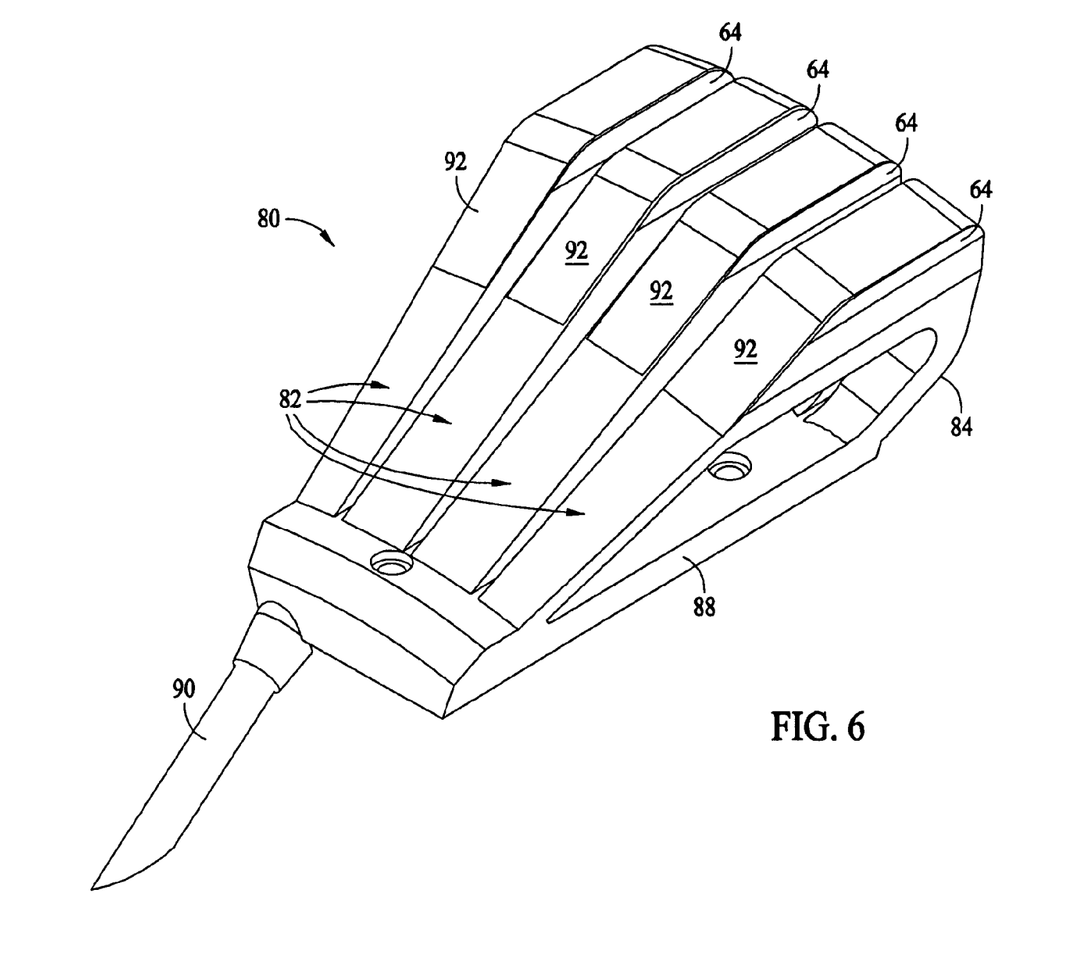
FIG. 6 is another perspective view of the sensor block configuration of FIG. 4 from another angle.

FIG. 4 is a side perspective view of a configuration of an assembly of a sensor block 80 that comprises four sensor bodies 50. Each sensor body 50 is supported by a spring support 82 that comprises or consists essentially of a material softer or less dense than the polyurethane used in sledge 64, or comprises or consists essentially of other suitable non-conductive material. Spring support 82 can be molded using suitable polyurethane epoxy, for example, so that entire sensor block 80 is a unitary component. An electrical cable 87 (partially shown in FIG. 5) from each sensor body 50 that communicates with microcontroller 58 and provides power and ground is embedded within a respective arm 84. These cables connect to a marshalling card 86, shown in the bottom view of FIG. 5. Marshalling card 86 is actually embedded in bottom section 88 of spring support 82, but is shown in FIG. 5 because in some configurations, bottom section 88 is transparent or semitransparent. Marshalling card 86 concatenates and packetizes data from all four sensor bodies 50 and provides this data for further processing through a power and data cable 90 that exits sensor block 80. A perspective view of sensor block 80 is shown in FIG. 6. In configurations of the present invention in which silicon carbide or other non-conductive material is used in a sledge 64 or in sensor cover 60 in its entirety, imperfections in a pipe wall that contact sloped surface 92 may cause spring support 82 to bend slightly to conform, but the portion of surface 92 that contacts this imperfection would be protected by the harder material out of which sledge 64 (or sensor cover 60) is made.

The single coil 54 together with the microcontroller 58 provide ID/OD discrimination used to assist in the determination of the location of the defect relative to the inside diameter or outside diameter of the pipeline 21. The microcontroller 58 measures the change in peak-to-peak amplitude of an induced waveform on a single coil 54. The peak-to-peak amplitude varies with its proximity to metallic objects; therefore if there is corrosion on the inside of the pipe, the microcontroller 58 senses the absence of metal, and if the corrosion is on the outside of the pipe there will be no measurable change in the single coil. Using the single coil 54 can in combination with the hall effect sensing device information, the microcontroller discern both magnitude and location of a defect.

Figure 7:
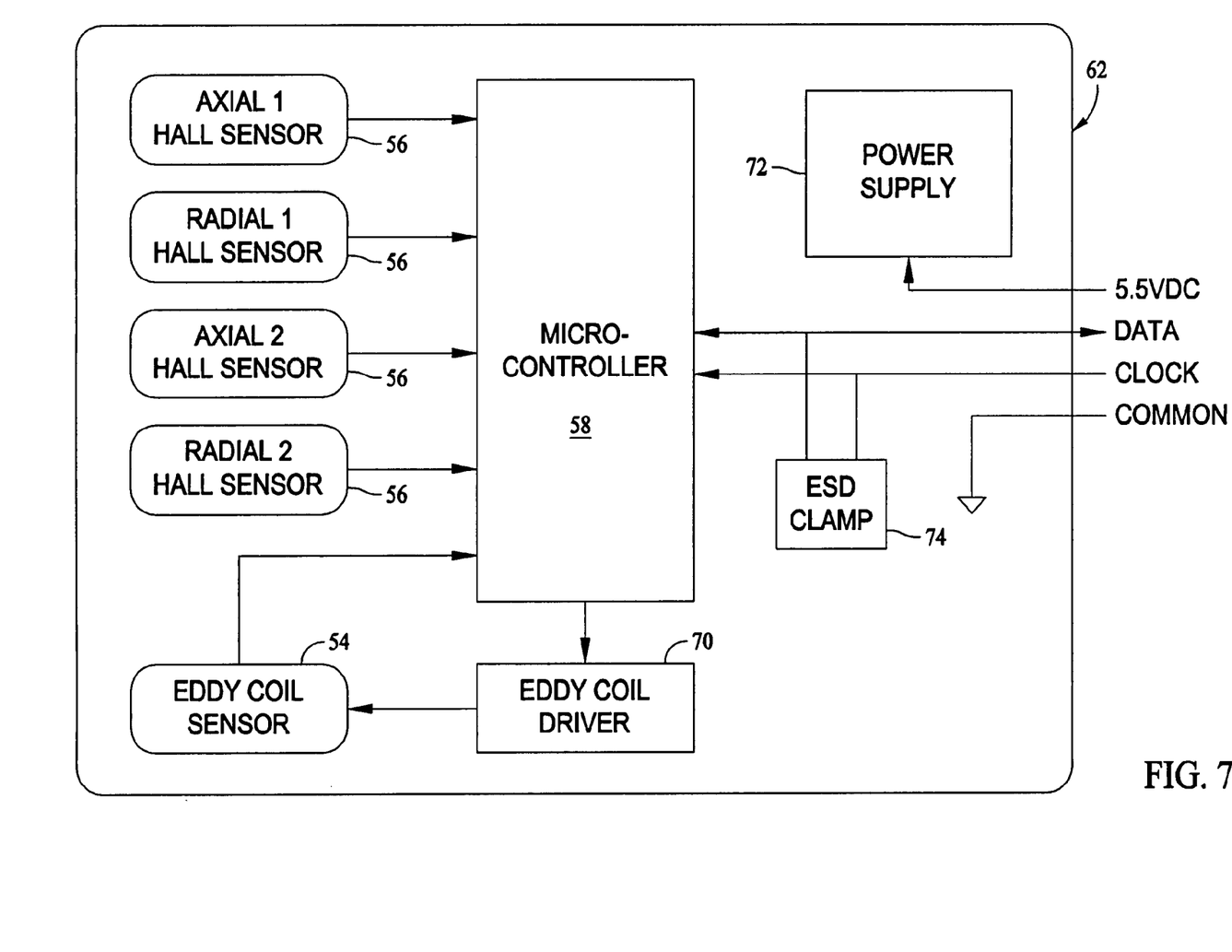
FIG. 7 is an electrical architectural overview of a configuration of a sensor head.

In some configurations and referring to FIG. 7, an architectural overview of a configuration of sensor head 62 used in some configurations of the present invention includes a plurality of Hall effect sensing devices 56 including two axial sensors and two radial sensors, a single eddy current coil 54, microcontroller or microprocessor 58, eddy current driver 70, a power supply 72, and an electrostatic discharge (ESD) clamp 74. Voltage, data, clock, and ground signals are provided via a cable. Microcontroller 58 manages digital to analog conversion functions, data telemetry, data processing, and eddy coil driver functions. Data and commands in some configurations are communicated between a host and sensor head 62 is over a half-duplex bidirectional synchronous data link supported directly by microcontroller 58 at a data rate of 1 megabit per second. Also in some configurations, electronics in sensor head 62 is a slave to the host. As a result, the host is responsible for managing the timing of command and data transfer operations. Data and clock signal lines are protected against ESD events by ESD clamp 74. Hall sensors 56 are, in some configurations, low noise linear Hall effect devices selected for appropriate flux sensitivity, turn-on time, and noise specifications, and are ratiometric to the power supply. In operation, Hall sensors 56 are normally turned off in some configurations, except during a sample cycle. At the start of a sample cycle, Hall sensors 56 are turned on, allowed to stabilize, sampled by an analog to digital converter in microcontroller 58, and then turned off. This sequence of events advantageously reduces the current consumption of sensor head 62.

Eddy coil 54 is used to measure a distance between sensor head surface 76 and pipeline wall 25 and in determining a fault location (ID or OD). In this use, microcontroller 58 excites eddy coil 54. A peak-to-peak measurement is made of a resulting waveform and the liftoff is derived from data contained in a calibration table stored in microcontroller 58.

The microcontroller single coil ID/OD sensing works as follows. A small coil 52 whose physical location is very close to the pipe wall (between 0 and 10 mm) is driven with a square wave signal from the microcontroller 58. The driving frequency of coil 52 is the free air resonant frequency of a tank circuit comprising coil 52 and a capacitor (not shown) on the same board as microcontroller 58. Coil 52 converts the electrical energy from the driving signal into a magnetic field which, when in range of the metallic object in question, induces an eddy current within the metallic object, resulting in a transfer of the energy into the metallic object. The driving frequency (and thus the capacitance of the on-board capacitor) is chosen to be high enough so that the metal is lossy at the driving frequency, yet low enough so that it can be adequately sampled by an analog to digital converter in microcontroller 58. Some configurations of the present invention utilize driving frequencies of 28 kHz to 40 kHz, for example, but higher and lower frequencies can be used as a design choice.

During the driving sequence of 4 to 5 square waveform pulses, for example, the amplitude of the drive signal is measured on a capacitively isolated side of the coil by the microcontroller 58. The amplitude of the high and low peaks are quantified by the analog to digital converter and subtracted. The net result is a peak to peak amplitude associated with the induced waveform in the coil 52, which amplitude is proportional to the coil's proximity to the target metallic object. Therefore, if the sensor body 50 is riding along a pipewall 21 and its distance increases (due to a pitting in the metal surface), a change in measured peak-to-peak amplitude signals that the sensor body 50 has lifted off from the metal surface. The liftoff is measured by means of measuring both the peak and trough of the induced waveform in response to the proximity of the coil to the metallic surface. Because the microcontroller 54 measures change in peak to peak amplitude, this measurement is immune to the effects of velocity (greater losses due to moving the sensor across a metallic surface—eddy current losses increase as a result).

Because the driving frequency of coil 52 is the resonant circuit of the tank circuit in free air, the effect of coil 52 passing over a defect is in the real domain rather than the imaginary. The amplitude is shifted measurably as a result. As a result, the effect of passing through a stray magnetic field can be cancelled out so that only the standoff from the pipe and/or the presence or absence of a defect is detected or recognized in some configurations of the present invention.

In some configurations of the present invention, one or more functions of sensor head 62 are overlapped to reduce overall cycle time. Also, some configurations ensure that data transmission is not active during acquisition of data from sensors 56 so that spurious electrical noise is reduced during the analog to digital conversion process.

It will thus be appreciated that the present invention provides advantages over sensor heads that use two coils, a pulser coil and a sensor coil, and decreases the size requirement of a sensor body and associated circuitry.

While the invention has been described in terms of various specific embodiments, those skilled in the art will recognize that the invention can be practiced with modification within the spirit and scope of the claims.

What is claimed is:

1. A sensor body for use in a pig for determining characteristics of a pipeline wall though which the pig passes, the sensor body comprising:
   a circuit board;
   a single coil wrapped around the circuit board;
   a microcontroller mounted to the circuit board and connected with the single coil for inducing a waveform on the coil to thereby create an eddy current in the pipeline wall adjacent the sensor body, and the microcontroller measuring changes in a characteristic of the induced waveform on the single coil that correspond to the presence of anomalies on an inside diameter of the pipeline wall, and
   a sensor body cover molded about the circuit board, the microcontroller and the single coil, and the sensor body cover consisting essentially of a wear resistant, nonconductive material that includes a polymer material.

2. The sensor body of claim 1 wherein the characteristic measured by microcontroller is changes in peak-to-peak amplitude of the induced waveform.

3. The sensor body of claim 1 further comprising a plurality of magnetic flux leakage measuring devices mounted on the circuit board and connected with the microcontroller for detecting flux leakage in the pipeline wall and the magnetic flux leakage devices each comprise a Hall effect sensing device.

4. The sensor body of claim 3 wherein the characteristic measured by microcontroller is changes in peak-to-peak amplitude of the induced waveform.

5. The sensor body of claim 4 wherein the wear resistant material comprises a polyurethane material filled with wear resistant particles.

6. The sensor body of claim 5 wherein the wear resistant particles comprise nonconductive particles.

7. The sensor body of claim 6 wherein the nonconductive particles comprise silicon carbide.

8. The sensor body of claim 1 wherein the wear resistant material comprises a polyurethane material filled with wear resistant particles.

9. The sensor body of claim 8 wherein the wear resistant particles comprise nonconductive particles.

10. The sensor body of claim 9 wherein the nonconductive particles comprise silicon carbide.

11. An instrument pig for analyzing anomalies in a wall of a pipeline, the pig comprising:
    a tow portion for moving the pig through the pipeline;
    an instrument portion for measuring the anomalies in the pipeline wall comprising:
    a plurality of arms disposed circumferentially around the instrument portion, each arm flexibly mounted on the instrument portion to allow the arm to move radially inwardly and radially outwardly to provide clearance for the pig in the event that it encounters obstructions as it travels through the pipeline;
    a sensor body mounted to each arm and comprising a circuit board, a single coil wrapped around the circuit board and a microcontroller mounted to the circuit board and connected with the single coil for inducing a waveform on the coil to thereby create an eddy current in the pipeline wall adjacent the sensor body, and the microcontroller measuring changes in a characteristic of the induced waveform on the single coil that correspond to the presence of anomalies on an inside diameter of the pipeline wall, and the sensor body comprising a sensor body cover molded about the circuit board, the microcontroller and the single coil, the sensor body cover consisting essentially of a wear resistant, nonconductive material including a polymer material, and
    magnets mounted on the arms for generating and transmitting a magnetic field through portions of the pipeline wall adjacent the sensor body; and,
    a data storage portion for storing data measured by the microcontroller.

12. The pig of claim 11 wherein the characteristic measured by the microcontroller is changes in peak-to-peak amplitude of the induced waveform.

13. The pig of claim 11 wherein the sensor body further comprises a plurality of magnetic flux leakage measuring devices mounted on the circuit board and connected with the microcontroller for detecting flux leakage in the pipeline wall.

14. The pig of claim 13 wherein the characteristic measured by the microcontroller is changes in peak-to-peak amplitude of the induced waveform and the magnetic flux leakage devices each comprise a Hall effect sensing device.

15. The pig of claim 14 wherein the wear resistant material comprises a polyurethane material filled with wear resistant particles.

16. The pig of claim 15 wherein the wear resistant particles comprise nonconductive particles.

17. The pig of claim 16 wherein the nonconductive particles comprises silicon carbide particles.

18. The pig of claim 11 wherein the wear resistant material comprises a polyurethane material filled with wear resistant particles.

19. The pig of claim 18 wherein the wear resistant particles comprise nonconductive particles.

20. The pig of claim 19 wherein the wear resistant particles comprise silicon carbide particles.

* * * * *